(12) United States Patent  
Parrish

(10) Patent No.: US 9,668,471 B2  
(45) Date of Patent: Jun. 6, 2017

(54) MANUFACTURE AND USE OF AGRICULTURAL SPRAY ADJUVANTS FOR HARD WATER CONDITIONS

(75) Inventor: Scott K. Parrish, Spokane, WA (US)

(73) Assignee: AGQUAM LLC, Spokane, WA (US)

( * ) Notice: Subject to any disclaimer, the term of this patent is extended or adjusted under 35 U.S.C. 154(b) by 0 days.

(21) Appl. No.: 10/853,781

(22) Filed: May 26, 2004

(65) Prior Publication Data

US 2005/0026780 A1     Feb. 3, 2005

Related U.S. Application Data

(60) Provisional application No. 60/473,540, filed on May 28, 2003.

(51) Int. Cl.
```
A01N 57/20      (2006.01)
H01H 1/0233     (2006.01)
A01N 25/10      (2006.01)
A01N 25/22      (2006.01)
A01N 25/32      (2006.01)
```

(52) U.S. Cl.
CPC ............. *A01N 25/10* (2013.01); *A01N 25/22* (2013.01); *A01N 25/32* (2013.01)

(58) Field of Classification Search
CPC .. C22C 32/0084; H01H 1/0233; A01N 57/20; A01N 2300/00
USPC ............................ 504/206; 424/405, 666, 718
See application file for complete search history.

(56) References Cited

U.S. PATENT DOCUMENTS

| | | | | |
|---|---|---|---|---|
| 5,078,782 A * | 1/1992 | Nielsen et al. | ............... | 504/135 |
| 5,116,401 A * | 5/1992 | Young | ............... | 504/196 |
| 5,302,579 A * | 4/1994 | Young | ............... | 504/206 |
| 5,389,598 A * | 2/1995 | Berk et al. | ............... | 504/206 |
| 5,683,958 A * | 11/1997 | Berger et al. | ............... | 504/364 |
| 5,877,112 A * | 3/1999 | Roberts et al. | ............... | 504/206 |
| 6,180,566 B1 * | 1/2001 | Nielsen et al. | ............... | 504/206 |
| 6,369,001 B1 * | 4/2002 | Jimoh | ............... | 504/118 |
| 6,541,424 B2 | 4/2003 | Roberts et al. | | |
| 6,803,345 B2 | 10/2004 | Herold et al. | | |
| 6,906,004 B2 | 6/2005 | Parrish et al. | | |
| 7,094,735 B2 | 8/2006 | Herold et al. | | |
| 2002/0107149 A1 | 8/2002 | Volgas et al. | | |
| 2002/0160916 A1 * | 10/2002 | Volgas et al. | ............... | 504/194 |
| 2003/0104943 A1 * | 6/2003 | Lennon | ............... | A01N 25/30 504/206 |
| 2003/0144147 A1 | 7/2003 | Herold et al. | | |
| 2003/0148889 A1 | 8/2003 | Herold et al. | | |
| 2003/0153461 A1 | 8/2003 | Parrish et al. | | |
| 2003/0153462 A1 | 8/2003 | Herold et al. | | |
| 2004/0127364 A1 | 7/2004 | Herold et al. | | |
| 2004/0167032 A1 | 8/2004 | Volgas et al. | | |
| 2005/0170967 A1 | 8/2005 | Parrish et al. | | |

(Continued)

OTHER PUBLICATIONS

The American Heritage Dictionary 1982 "include" 3 pages.*

(Continued)

*Primary Examiner* — Ernst V Arnold  
(74) *Attorney, Agent, or Firm* — Swanson & Bratschun, L.L.C.

(57) ABSTRACT

The invention pertains to a method for manufacture and use of pesticides or agricultural spray adjuvants that counteracts the effects of hard water cat ions on anionic pesticides when applied in water spray solutions.

9 Claims, 2 Drawing Sheets

Formula 21-1 as Compared to AMS for the Reduction of Hardwater Tie Up of Glyphosate Salt. As Measured by Percent Control of Annual Bluegrass. Zinc acetate added as the complexing Anion. V/v =Volume to Volume

(56) References Cited

U.S. PATENT DOCUMENTS

2006/0205601 A1     9/2006    Herold et al.
2006/0270557 A1    11/2006    Volgas et al.

OTHER PUBLICATIONS

Cox (Glyphosate Factsheet Journal of Pesticide Reform 2000, 108(3), part 1 and part 2).*
Petroff R. Water Effects on Pesticide Performance Apr. 12, 2003. [online] retrieved from the Internet on Apr. 13, 2008; retrieved from http://web.archive.org/web/20030412083321/http://www.co.fergus.mt.us/weed/Water+Effects+on+Pesticide+Efficacy.htm.*
Carlson et al. (Weed Science; 1984, 32: p. 841).*
Nalewaja et al. (Weed Science; 1991, 39: p. 622).*
SAG 10 [online] retrieved on May 16, 2016 from: http://www.hazard.com/msds/f2/bxn/bxndk.html; 3 pages.*
Thomas, A. 2000. Fats and Fatty Oils. Ullmann's Encyclopedia of Industrial Chemistry. 72 pages.*
BSCS Biology. 2002 Rutgers University Press; 22.17: 1 page.*
Williams et al. (Regulatory Toxicology and Pharmacology 2000, 31, 117-165).*
Thelen et al. The Basis for the Hard-Water Antagonism of Glyphosate Activity (1995) Weed Science 43 (4):541-548.
Nalewaja and Matysiak, Influence of Diammonium Sulfate and Other Salts on Glyphosate Phytotoxicity (1993) Pesticide Sci. 38:77-84.
Hartzler, Role of AMS with glyphosate products. (Feb. 2001) R. Extension Bulletin, Iowa State University.
David Wm. Reed. (1996) Water Quality Management for Greenhouse Production, Ball Publishing, Batavia, IL, ISBN: 1-883052-12-2.
Bohn et al. (1985) *Soil Chemistry*, 2nd Ed, Wiley Interscience pp. 241-243.
Water Chemistry As It Applies to pH and Alkalinity Greenhouse Product News (Feb. 1999).
Reeves Petroff "Water Effects on Pesticide Performance" Pesticide Education Specialist, Montana State University (downloaded from internet).
Reeves Petroff "Water Quality and Pesticide Performance" Pesticide Education Specialist, Montana State University Extension Service (Updated Feb. 28, 2000).

* cited by examiner

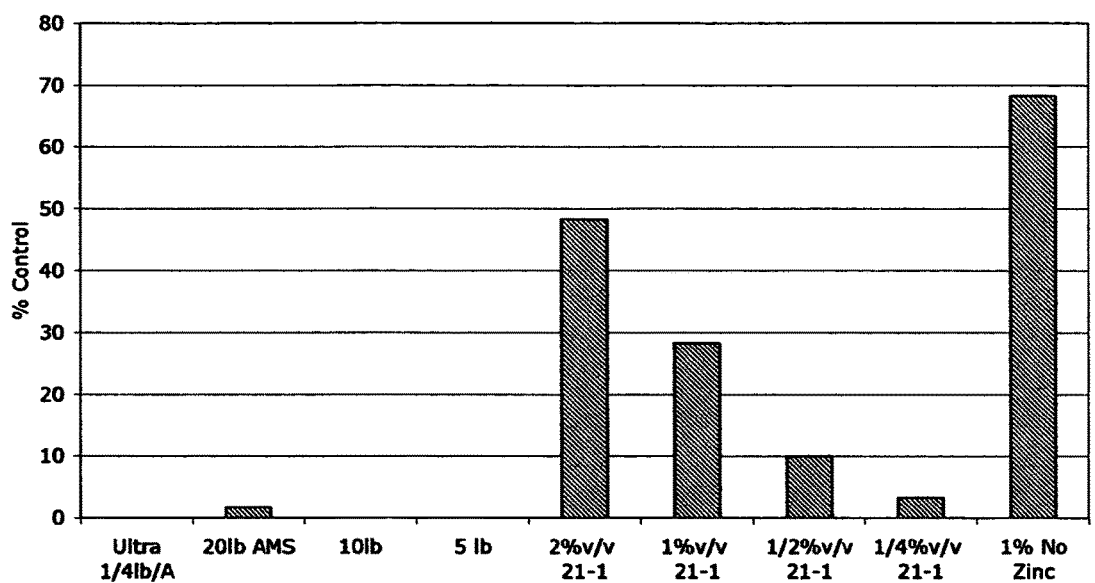
Figure 1. Formula 21-1 as Compared to AMS for the Reduction of Hardwater Tie Up of Glyphosate Salt. As Measured by Percent Control of Annual Bluegrass. Zinc acetate added as the complexing Anion. V/v =Volume to Volume

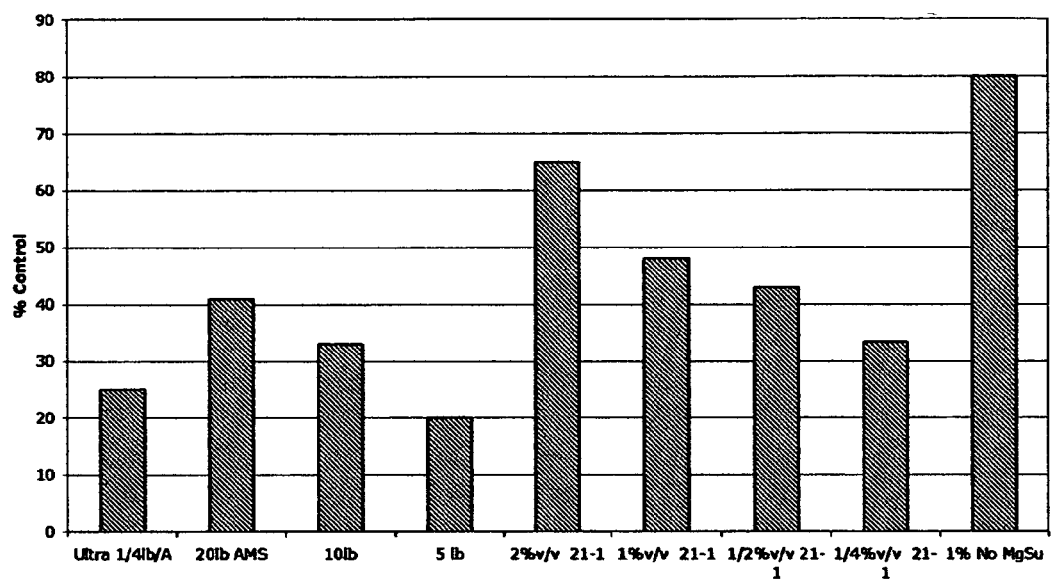
Figure 2. The Effect of Formula 21-1 on Restoring the Activity of Glyphosate as Demonstrated by Percent Control of Annual Bluegrass as Compared to Ammonium Sulfate (AMS). Magnesium Sulfant (MgSu) was Added to the Mixture to Simulate Hard Water Cations.

MANUFACTURE AND USE OF AGRICULTURAL SPRAY ADJUVANTS FOR HARD WATER CONDITIONS

BACKGROUND OF THE INVENTION

It is know that the addition of fertilizer blends in the application of many pesticides will improve the performance of the active ingredient. The current market standard is ammonium sulfate (AMS). It is speculated that one of the reasons for this is that the anion portion of the fertilizer blend, sulfate, will associate with the hard water cation. Therefore the anion or acidic pesticide will not associate with the hard water cation and be more available for uptake into the target species. "Data suggest hard-water cations, such as $Ca^{+2}$ and $Mg^{+2}$ present in the spray solution can greatly reduce the efficacy of glyphosate. These cations potentially compete with the isopropylamine in the formulation for association with the glyphosate anion."[1] Hard water with cations present in a concentration range higher than 100 ppm-150 ppm have been shown to cause a decrease in effectiveness of many pesticides.[2] It is thought by some authors that the reason for the reduced activity with glyphosate is that the glyphosate anion will form insoluble salts with many hard water cations. This would be true for many anions pesticides including glyphosate, 2,4-D and glufosinate. This would also be true for acidic herbicides that could become anionic depending upon pH an example of this would be sethoxydim.[3,4]

This information has lead to the common practice of glyphosate and other anionic pesticides being applied in the presence of ammonium sulfate (AMS) in the spray mixture. However, in other industries a common practice to remove hard water cations such as $Ca^{+2}$, $Fe^{+2}$, $Mg^{+2}$ and $Zn^{+2}$ is via acidic reaction with mineral acids such as nitric and sulfuric acid.[5] This technology has been adapted to cation management in both soil and irrigation water and is based on the "Langelier index."[6] Cation management using phosphoric acid as a spray mixture has been tried with limited success as compared to spray mixtures containing AMS. It is speculated that the reason that phosphoric acid products do not work s well as AMS is that phosphoric acid does not completely dissociate when added to water at normal spray mixture pH ranges. It is therefore less reactive to the hard water cations than originally thought by the creators of these products. Other mineral acids were considered to be impractical in pesticide applications because small mistakes or misuse with these powerful acids will drop the pH of a spray solution in the spray tank below the pKa of many anionic pesticides, including glyphosate. If this occurs the pesticide will precipitate and will no longer be sprayable.

An idea was formed that mineral acid management of hard water cations would be much more efficient than AMS management of hard water cations if a mineral acid that completely dissociates in water could be used and a reliable delivery system could be devised or discovered for these types of acids. The three driving factors for this idea are: 1) Much less acid is needed to tie up the hard water cations than AMS. The amount of AMS recommended is 17.5 lb per 100 gallons of waters with 150-250 ppm hard water cations[4], whereas only 1.3 oz of sulfuric acid per 100 gallons is needed to neutralize the 150-250 ppm hard water cations.[7] 2) Sulfuric acid and nitric acid will form semi and insoluble salts with the hard water cations, whereas AMS has only been shown to associate with these cations. It is unlikely that they form salts.[3] 3) AMS as a salt is hard to dissolve into the spray solutions which makes it difficult to work with, whereas, acids are completely miscible in water.

1. The basis for the hard-water antagonism of glyphosate activity. Thelen, K. D. Weed Science v.43 (4) 1995 pp. 541-548.
2. Weed Science Principles and Application. Anderson, W P third edition, West Publishing Co. Minneapolis Minn.
3. Nalewaja, J. D. and R. Matysiak. 1993. Pesticide Sci. 38:77-84.
4. Role of AMS with glyphosate products. Hartzler, R. Extension Bulletin, Iowa State University.
5. David Wm. Reed. 1996. Water, media and nutrition for greenhouse crops. Ball Publishing, Batavia, IL, ISBN: 1-883052-12-2.
6. Bohn H. L., McNeal, B. L., O'Connor, G. A., Soil Chemistry, A Wiley-Interscience Pub. John Wiley & Sons, New York, N.Y.
7. Greenhouse Product News February '99

SUMMARY OF THE INVENTION

A mixture of strong mineral acids which would completely dissociate in water, including but not limited too; nitric acid, hydrochloric acid, sulfuric acid, perchloric acid, and a polymer, preferred would be cationic, that is formulated as an agricultural spray adjuvant. The polymer in the formulation acts as a slow release mechanism for the acid. Polymeric forces on the mineral acid give the grower a practical mechanism for using mineral acid to counteract hard water cations. The adjuvant when mixed in a agricultural spray solution would act to tie up the hard water cations thus protecting any anionic pesticides, defoliants or plant growth regulators from reacting with the hard water cations such as Ca++, Mg++, Fe++ and becoming less effective as an agricultural chemicals. Thus the spray adjuvant would act to increase the apparent efficacy of the active ingredient being applied.

BRIEF DESCRIPTION OF THE DRAWINGS

FIG. 1 shows the effect of Formula 21-1 relative to AMS on the reduction of hardwater tie up of glyphosate salt as a percent control of annual bluegrass.

FIG. 2 shows the effect of Formula 21-1 relative to AMS on restoring the activity of glyphosate under hard water conditions as a percent control of annual bluegrass.

DETAILED DESCRIPTION OF THE INVENTION

Strong mineral acids were added to polymers in an attempt to deliver a controlled amount of acid into a spray solution. The acid would act as a "hard water cation scavenger". The mixture would be an agronomic spray "hard water scavenger system". In the preferred example sulfuric acid was added to tallow amine. Heat was given off indicating some reaction. However, pH measurements of spray mixtures taken before and after the addition of the "hard water scavenger system" shows that free acid still existed.

Knowing that any potential spray solution which could be contemplated would have to stay above a pH of which is higher that the pKa of most anionic pesticides. Differing mixtures of several examples where made up. Table 1, Table 2, Table 3. It was thought that this would be a more efficient method to condition the spray waters than current practice of using Ammonium Sulfate (AMS). However, the mixture would have to remain stable, not drop the pH below the pKa of anionic pesticides and work as well as or better than AMS.

The efficiency would be gained by replacing large bags of dry AMS (17.5 lbs/100 gallons spray solution) or large volumes (5 gallon/100 gallons spray solution) of liquid AMS with 1 quart to 1 gallon per 100 gallons of spray solution with this kind of product. Also this liquid product would go into solution much faster than the current AMS goes into solution adding even more efficiency.

It was discovered that cationic macro molecules would make a stable mix with sulfuric acid. Also, cationic surfactant would act as a system that would deliver enough free acid to tie up hard water cations. While at the same time maintain the pH of the spray water above the pKa of the active ingredient being sprayed thus increasing the efficacy of the pesticide.

It was surprising to discover that these mixtures increased or maintained the efficacy of anionic pesticides under hard water conditions much better than the current practice of adding Ammonium Sulfate (FIG. 1 and FIG. 2).

TABLE 1

| Example 1 | |
|---|---|
| Formula 21-1 | |
| Water | 65.9%/wt |
| Tallow Am 3780 | 30.0 |
| SAG 10 | 0.1 |
| 93% Sulfuric | 4.0 |

TABLE 2

| Example 2 | |
|---|---|
| Formula 21-2 | |
| Water | 45.9%/wt |
| Tallow Am 3780 | 50.0 |
| SAG10 | 0.1 |
| 93% Sulfuric | 4.0 |

TABLE 3

| Example 3 | |
|---|---|
| INGREDIENT | %/WT |
| Diethylene Glycol | 17.80 |
| NP-10 | 50.00 |

TABLE 3-continued

| Example 3 | |
|---|---|
| INGREDIENT | %/WT |
| AU391 | 30.00 |
| 93% Sulfuric Acid | 2.00 |
| SAG 10 [ | 0.20 |

I claim:

1. A water soluble glyphosate composition consisting essentially of:

(a) an aqueous glyphosate solution consisting of glyphosate or salt thereof as the sole pesticide active ingredient; (b) a mixture consisting of an effective amount of a mineral acid selected from the group consisting of sulfuric acid and hydrochloric acid and 30-50 wt percent of a polyamine surfactant selected from the group consisting of tallow amine ethoxylate and coco amine ethoxylate combined in an agricultural spray solution;

wherein said composition does not contain ammonium sulfate (AMS); and wherein said composition consists of a ratio of 1 quart to 2 gallons of (b) to 100 gallons of (a); and wherein said composition has a pH above the $PKa_2$ of glyphosate, and wherein better herbicidal efficacy is provided in comparison to 5-20 pounds AMS per 100 gallons of (a).

2. The composition as claimed in claim 1, wherein said acid has the ability to completely or nearly completely dissociate in water and react with cations.

3. The composition as claimed in claim 1, wherein said polyamine surfactant is tallow amine ethoxylate.

4. A water soluble glyphosate composition of claim 1 wherein said composition consists of a ratio of 1 quart to 1 gallon of (b) to 100 gallons of (a).

5. The composition as claimed in claim 1, wherein said polyamine surfactant is coco amine ethoxylate.

6. The composition as claimed in claim 3, wherein said mineral acid is sulfuric acid.

7. The composition as claimed in claim 3, wherein said mineral acid is hydrochloric acid.

8. The composition as claimed in claim 5, wherein said mineral acid is sulfuric acid.

9. The composition as claimed in claim 5, wherein said mineral acid is hydrochloric acid.

* * * * *